United States Patent
Jiang et al.

(10) Patent No.: US 12,040,047 B2
(45) Date of Patent: Jul. 16, 2024

(54) VALIDATION METHODS AND SYSTEMS FOR SEQUENCE VARIANT CALLS

(71) Applicant: ILLUMINA, INC., San Diego, CA (US)

(72) Inventors: Tingting Jiang, San Diego, CA (US); Chen Zhao, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 1093 days.

(21) Appl. No.: 16/206,552

(22) Filed: Nov. 30, 2018

(65) Prior Publication Data

US 2019/0206510 A1  Jul. 4, 2019

Related U.S. Application Data

(60) Provisional application No. 62/593,095, filed on Nov. 30, 2017.

(51) Int. Cl.
*G16B 20/20* (2019.01)
*G16B 30/00* (2019.01)
*G16B 40/00* (2019.01)

(52) U.S. Cl.
CPC .............. *G16B 20/20* (2019.02); *G16B 30/00* (2019.02); *G16B 40/00* (2019.02)

(58) Field of Classification Search
CPC ......... G16B 20/20; G16B 40/00; G16B 30/00
USPC .......................................................... 702/20
See application file for complete search history.

(56) References Cited

U.S. PATENT DOCUMENTS

| 6,172,218 B1 | 1/2001 | Brenner |
| 6,306,597 B1 | 10/2001 | Macevicz |
| 6,969,488 B2 | 11/2005 | Bridgham et al. |
| 7,001,792 B2 | 2/2006 | Sauer et al. |
| 7,057,026 B2 | 6/2006 | Barnes et al. |
| 2005/0100900 A1 | 5/2005 | Kawashima et al. |
| 2006/0188901 A1 | 8/2006 | Barnes et al. |
| 2006/0240439 A1 | 10/2006 | Smith et al. |

(Continued)

FOREIGN PATENT DOCUMENTS

| JP | 2017506875 A | 3/2017 |
| WO | 2005/065814 A1 | 7/2005 |

(Continued)

OTHER PUBLICATIONS

Thomas Blomquista, Erin L. Crawfordb, Jiyoun Yeob, Xiaolu Zhangb, James C. Willey: "Control for stochastic sampling variation and qualitative sequencing error in next generation sequencing", Biomolecular Detection and Quantification 5 (2015) 30-37 (Year: 2015).*

(Continued)

*Primary Examiner* — Russell S Negin
*Assistant Examiner* — Guozhen Liu
(74) *Attorney, Agent, or Firm* — Fletcher Yoder P.C.

(57) ABSTRACT

Presented herein are techniques for identifying and/or validating sequence variants in genomic sequence data. The techniques include generating an error rate reflective of sequence errors present in the genomic sequence data. The error rate may be used to validate potential sequence variants. The error rate may be based on errors identified during consensus sequence confirmation for sequence reads associated with individual unique molecular identifiers.

18 Claims, 11 Drawing Sheets

(56) References Cited

U.S. PATENT DOCUMENTS

| | | | |
|---|---|---|---|
| 2006/0281109 A1 | 12/2006 | Barr Ost et al. | |
| 2007/0166705 A1 | 7/2007 | Milton et al. | |
| 2009/0026082 A1 | 1/2009 | Rothberg et al. | |
| 2009/0088327 A1 | 4/2009 | Rigatti et al. | |
| 2009/0127589 A1 | 5/2009 | Rothberg et al. | |
| 2010/0137143 A1 | 6/2010 | Rothberg et al. | |
| 2010/0282617 A1 | 11/2010 | Rothberg | |
| 2014/0336999 A1* | 11/2014 | Kumar .................. | G16B 20/20 703/11 |
| 2015/0044687 A1 | 2/2015 | Schmitt et al. | |
| 2015/0275289 A1 | 10/2015 | Otwinowski et al. | |
| 2015/0324519 A1 | 11/2015 | Liu | |
| 2016/0319345 A1 | 11/2016 | Gnerre et al. | |
| 2018/0202003 A1 | 7/2018 | Lo et al. | |

FOREIGN PATENT DOCUMENTS

| | | |
|---|---|---|
| WO | 2006/064199 A1 | 6/2006 |
| WO | 2007/010251 A1 | 1/2007 |
| WO | 2007010252 | 1/2007 |
| WO | 2008/041002 | 4/2008 |
| WO | 2016040901 A1 | 3/2016 |
| WO | 2017151524 A1 | 9/2017 |

OTHER PUBLICATIONS

Kou R, Lam H, Duan H, Ye L, Jongkam N, Chen W, et al. (2016) Benefits and Challenges with Applying Unique Molecular Identifiers in Next Generation Sequencing to Detect Low Frequency Mutations. PLoS One 11(1): e0146638. (Year: 2016).*

PCT/US18/63372 , "Interntaional Search Report", dated Mar. 18, 2019, 1-15.

Cockroft , et al., "A single-molecule nanopore device detects DNA polymerase activity with single-nucleotide resolution", J. Am. Chem. Soc, 130(3), Jan. 23, 2008, 818-820.

Healy, Ken , "Nanopore-based single-molecule DNA analysis", Nanomed. 2(4), 2007, 459-481.

Korlach , et al., "Selective aluminum passivation for targeted immobilization of single DNA polymerase molecules in zero-mode waveguide nanostructures", PNAS, vol. 105 No. 4, 2008, 1176-1181.

Levene , et al., "Zero-Mode Waveguides for Single-Molecule Analysis at high concentrations", Science 299, 2003, 682-686.

Lundquist , et al., "Parallel confocal detection of single molecules in real time", Opt. Lett. 33(9), 2008, 1026-1028.

Soni , et al., "Progress toward Ultrafast DNA Sequencing Using Solid-State Nanopores", Clin Chem, 53(11), 2007, 1996-2001.

Examination Report No. 2 for AU Application No. 2018375785 dated Apr. 9, 2021, 7 pgs.

* cited by examiner

| SAMPLE | ERROR RATE | SENSITIVITY (LIKELIHOOD) | SPECIFICITY (LIKELIHOOD) | SENSITIVITY (DEFAULT) | SPECIFICITY (DEFAULT) |
|---|---|---|---|---|---|
| Lot30_T5_rep3 | 3.46E-05 | 0.880841121 | 0.99971514 | 0.892523364 | 0.99945117 |
| Lot30_T5_rep1 | 3.35E-05 | 0.883177757 | 0.999737929 | 0.894859813 | 0.99947206 |
| Lot30_T5_rep2 | 3.30E-05 | 0.873831776 | 0.999741727 | 0.885514019 | 0.999416987 |
| Lot31_T5_rep2 | 3.24E-05 | 0.885514019 | 0.99971514 | 0.897196262 | .0999502445 |
| Lot31_T5_rep1 | 3.21E-05 | 0.890186916 | 0.999734131 | 0.880841121 | 0.999504344 |
| Lot31_T5_rep3 | 3.18E-05 | 0.873831776 | 0.999743626 | 0.873831776 | 0.999565114 |

FIG. 10

VALIDATION METHODS AND SYSTEMS FOR SEQUENCE VARIANT CALLS

CROSS REFERENCE TO RELATED APPLICATIONS

The present application claims priority to U.S. Provisional Application No. 62/593,095, entitled "VALIDATION METHODS AND SYSTEMS FOR SEQUENCE VARIANT CALLS" and filed Nov. 30, 2017, the disclosure of which is incorporated herein by reference for all purposes.

BACKGROUND

The present disclosure relates generally to the field of data related to biological samples, such as sequence data. More particularly, the disclosure relates to techniques for validating sequence variant calls based on sequencing data acquired during sequencing operations.

Genetic sequencing has become an increasingly important area of genetic research, promising future uses in diagnostic and other applications. In general, genetic sequencing involves determining the order of nucleotides for a nucleic acid such as a fragment of RNA or DNA. Next-generation sequencing (NGS) offers an ability to identify sequence variants in a biological sample. The NGS test includes a DNA workflow for the identification of single nucleotide variants (SNVs), small insertions and deletions (indels), multiple nucleotide variants (MNVs), gene amplifications (CNVs). The NGS test also includes a RNA workflow for the identification of splice variants and gene fusions. A sequence variant is identified when a sample nucleic acid sequence is determined to different from a reference or baseline sequence at one or more base pair positions along the sequence. Identification of one or more sequence variants may in turn be used to characterize a patient sample, diagnose a clinical condition, and/or classify disease (e.g., cancer) progression.

However, validation of sequence variants is complex. Certain sequencing techniques experience false positives in connection with variant calling. For example, the technique may incorrectly determine that a variant is present in a sample sequence at a particular location (base pair) and/or incorrectly identify the type of variant, which leads to false positives in identified sequence variants. False positive sequence variants may be the result of error introduced into the sample itself at the sample preparation stage and/or may be the result of systematic errors introduced during amplification or sequence acquisition. Further, certain types of samples (e.g., FFPE samples) may be more prone to error. A need remains for sequencing methods and systems that can accurately identify DNA variants while reducing a number of false positives in an efficient and cost-effective manner.

Definitions

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. As used herein, the following terms have the meanings indicated.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some embodiments, a site may be a residue, a sequence tag, or a segment's position on a sequence. The term "locus" may be used to refer to the specific location of a nucleic acid sequence or polymorphism on a reference chromosome.

The term "sample" or "biological sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, genomic sequence, sample sequence, reference sequence, and the like). Other terms, such as "allele," may be given different labels to differentiate between like objects.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows: (a) generate clusters of nucleic acids; (b) linearize the nucleic acids; (c) hybridize a first sequencing primer and carry out repeated cycles of extension, scanning and deblocking, as set forth above; (d) invert the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome", "reference sequence", or "baseline sequence" refers to any particular known genome sequence, whether partial or complete, of any organism which may be used to reference identified sequences from a subject and relative to which one or more sequence variants may be determined. For example, a reference genome used for human subjects as well as many other organisms is found at the National Center for Biotechnology Information at ncbi.nlm.nih.gov. A "genome" or genomic sequence refers to the complete genetic information of an organism or virus, expressed in nucleic acid sequences. A genome includes both the genes and the non-coding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about $10^7$ times larger. In one example, the reference genome sequence is that of a full length human genome. In another example, the reference genome sequence is limited to a specific human chromosome. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In another embodiment, the reference sequence may include sequence information for a subset of the genome that aligns with a targeted sequencing panel. In various embodiments, the reference genome is a consensus sequence or other combination derived from multiple individuals. That is, the reference sequence may be a hypothetical or representative sequence. However, in certain applications, the reference sequence may be taken from a particular individual. In one embodiment, the reference sequence is a normal sequence and the sample of interest is a matched tumor sequence from the same individual. In another embodiment, a reference sequence is taken at a first time point and the sample sequence is taken at a second, subsequent, time point. As provided herein, a reference sequence may be used as a basis relative to which sequence variants are determined. The reference sequence may be provided as a stored data file that may be accessed and/or operated on according to processor-executed instructions. Further, a system as provided herein may include a stored set of different reference sequences that may be selected based on user input related to the sample of interest and/or the sequencing type (whole genome, targeted sequencing). In one embodiment, a sample from an individual user may sequenced, and an appropriate reference sequence may be accessed (e.g., from a cloud computing environment) as an input to a sequence variant operation on the genomic sequence data.

The term "read" or "sequence read" refers to a collection of sequence data that describes a fragment of a nucleotide template sample or reference. The fragment may be a fragment generated during sample preparation. The term "read" may refer to a sample read (from a biological sample of interest) and/or a reference read (a sequence read acquired as part of sequencing a reference sample). A read may represent a short sequence of contiguous base pairs in the sample or reference. The read may be represented symbolically by the base pair sequence (in ATCG) of the sample or reference fragment. It may be stored in a memory device and processed as appropriate to determine whether the read matches or has differences relative to a reference sequence or meets other criteria. A sequence read may be obtained directly from a sequencing apparatus or may be accessed from stored sequence information concerning the sample. In some cases, a read is a DNA sequence of sufficient length (e.g., at least about 25 bp) that can be used to identify a larger sequence or region, e.g., that can be aligned, e.g., stitched together, and specifically assigned to a chromosome or genomic region or gene as part of genome assembly. The terms "sample read", "sample sequence" or "sample fragment" refer to sequence data of a genomic sequence of interest from a sample. For example, in one embodiment, the sample read includes sequence data from a PCR amplicon having a forward and reverse primer sequence. The sequence data can be obtained from any appropriate sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) or collapsed sequence derived from multiple sample reads.

Next-generation sequencing (NGS) methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, an Illumina sequencing method using SOLiD sequencer generates nucleic acid reads of about 50 bp. In another example, Ion Torrent Sequencing generates nucleic acid reads of up to 400 bp and 454 pyrosequencing generates nucleic acid reads of about 700 bp. In yet another example, single-molecule real-time sequencing methods may generate reads of 10,000 bp to 15,000 bp. Therefore, in certain embodiments, the reads as provided herein have a length of 30-100 bp, 50-200 bp, or 50-400 bp.

The terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). In some cases, an alignment additionally indicates a location in the reference sequence where the read or tag maps to. For example, if the reference sequence is the whole human genome sequence, an alignment may indicate that a read is present on a particular chromosome, and may further indicate that the read is on a particular strand and/or site of the chromosome.

The term "variant" or "sequence variant" refers to a nucleic acid sequence that is different from a reference sequence. Typical nucleic acid sequence variant includes without limitation single nucleotide polymorphism (SNP), short deletion and insertion polymorphisms (Indel), copy number variation (CNV), microsatellite markers or short tandem repeats and structural variation. Variants may also occur at homopolymer regions with at least 4 repetitive nucleotides, e.g., AAAA, GGGG, CCCC, TTTT. Somatic variant calling, sequence variant calling, or variant calling as provided herein refers to identification and/or validation of sequence variants present in a sample of interest. In one embodiment, variant calling may be used to characterize cancer progression. For example, a single nucleotide variation might be seen in a certain percentage of the reads covering a given base.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant frequency" or "variant allele frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some embodiments, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more embodiments may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some embodiments, the count score may be a value that is equal to the read count. In other embodiments, the count score may be based on the read count and other information. For example, a count score may be based on the read count for a particular allele of a genetic locus and a total number of reads for the genetic locus. In some embodiments, the count score may be based on the read count and previously-obtained data for the genetic locus. In some embodiments, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele. A "likelihood score" is a score per variant site given the error rate estimate according to the disclosed embodiments, and may also be based in part on an alternative read count (count of number of variant sample reads) and a total read count for the variant site in question. In one embodiment, an error rate is based on a total count of sequence reads determined to have sequence errors as provided herein. A biological sample having a high total count may be considered to have a higher error rate than another biological sample having a lower total count The terms "coverage", "sequence coverage", "read coverage", or "fragment coverage" refer to a count or other measure of a number of sample reads for the same fragment of a sequence. A sequence read count may represent a count of the number of reads that cover a corresponding fragment. Alternatively, the coverage may be determined by multiplying the read count by a designated factor that is based on historical knowledge, knowledge of the sample, knowledge of the locus, etc.

"Allele quality" (AQ) is the quality score of observed allele frequency in test sample against baseline or reference samples.

Unique molecular indices or unique molecular identifiers (UMIs) are sequences of nucleotides applied to or identified in nucleic acid molecules that may be used to distinguish individual nucleic acid molecules from one another. UMIs may be sequenced along with the nucleic acid molecules with which they are associated to determine whether the read sequences are those of one source nucleic acid molecule or another. The term "UMI" may be used herein to refer to both the sequence information of a polynucleotide and the physical polynucleotide per se. UMIs are similar to bar codes, which are commonly used to distinguish reads of one sample from reads of other samples, but UMIs are instead used to distinguish nucleic acid template fragments from another when many fragments from an individual sample are sequenced together. The UMIs may be single or double-stranded, and may be at least 5 bases, at least 6 bases, at least 7 bases, at least 8 bases, or more. In certain embodiments, the UMIs are 5-8 bases, 5-10 bases, 5-15 bases, 5-25 bases, 8-10 bases, 8-12 bases, 8-15 bases, or 8-25 bases in length, etc. Further, in certain embodiments, the UMIs are no more than 30 bases, no more than 25 bases, no more than 20 bases, no more than 15 bases in length. It should be understood that the length of the UMI sequences as provided herein may refer to the unique/distinguishable portions of the sequences and may exclude adjacent common or adapter sequences (e.g., p5, p7) that may serve as sequencing primers and that are common between multiple UMIs having different identifier sequences.

BRIEF DESCRIPTION

The present disclosure provides a novel approach for detection of sequence variants and/or validation of identified sequence variants in a biological sample. The disclosed techniques harness sequence information used for sequence assembly and/or analysis to extract a sequence data error rate that is characteristic of overall sequencing errors present in the sequence data. Such techniques enhance or may be used in conjunction with other techniques for reducing error. For example, certain techniques involve reducing error in a read group, a group of sequence reads that all include or are associated with the same unique molecular identifier (UMI). As provided herein, the present techniques track, and in some embodiments characterize, errors identified within multiple individual read groups of genomic sequence data to generate a characteristic error rate for the genomic sequence data. The error rate may in turn be used to determine if individual potential sequence variants are valid. For example, for genomic sequence data having a relatively high overall error rate, potential sequence variants may be subject to more stringent read coverage thresholds before being validated. For genomic sequence data having a relatively low overall error rate, lower read coverage thresholds may be permitted in such samples to validate an individual potential sequence variant. In this manner, the validation of sequence variants may be dependent on the quality of the genomic sequence data as exhibited by the error rate.

The present techniques improve efficiency and accuracy in identification and validation of sequence variants. In certain embodiments, the present techniques permit variant calling even in the context of low read coverage and/or the absence of a qualified duplex strand for samples identified as having appropriate error rates. In certain embodiments, the present techniques reduce a number of identified false positive sequence variants by identifying genome sequence data, or sites within such data, likely to contain false positives. Further, the present techniques harness data typically disregarded during consensus sequence determination to extract meaningful information, thereby improving the efficiency of variant calling. That is, rather than simply eliminating outlier sequences within a read group, the present techniques identify these eliminated sequences to determine the number and, in embodiments, nature of the sequence errors present. Based on an overall or global error rate for all sequencing errors or for certain types of sequencing errors in the sequence data of a particular sample, individual variants may be validated. The validation conditions may be set based on the error rate for each type of change. If a particular sample is associated with a high rate of sequencing errors of a certain type of nucleotide change (e.g., C to T), identified variants with alternative C to T sequences may have more stringent validation conditions relative to variants with alternative sequences associated with a lower error rate within the sample.

As such, a characteristic error rate (or error rates) for an individual sample may be determined on a sample-to-sample basis. While the presence of errors in genomic sequence data may be related to a variety of error sources that are complex to predict, the disclosed embodiments facilitate determination of more accurate sequence variant information in a customized manner to account for such error sources and error variability.

In an embodiment, a computer-implemented method is provided. The method is performed under control of a processor executing instructions. The method includes the step of receiving genomic sequence data of a biological sample, wherein the genomic sequence data comprises a plurality of sequence reads, each sequence read being associated with a unique molecular identifier of a plurality of unique molecular identifiers. The method also includes the step of identifying errors in the genomic sequence data based on sequence disagreement within a first subset of the plurality of sequence reads associated with a first unique molecular identifier, sequence disagreement between the first subset and a second subset of the plurality of sequence reads having a second unique molecular identifier complementary to the first unique molecular identifier, or both, to generate an error rate of the genomic sequence data. The method also includes the steps of identifying a plurality of potential sequence variants in the genomic sequence data relative to a reference sequence; classifying false positive sequence variants of the plurality of potential sequence variants based on the error rate of the genomic sequence data; and eliminating the false positive sequence variants from the plurality of potential sequence variants to yield a plurality of sequence variants.

In an embodiment, a computer-implemented method is provided. The method is performed under control of a processor executing instructions. The method includes the step of receiving genomic sequence data of a first biological sample, wherein the genomic sequence data comprises a plurality of sequence reads, each sequence read being associated with a unique molecular identifier of a plurality of unique molecular identifiers. The method also includes the step of identifying first sequence differences within a first subset of the plurality of sequence reads associated with a first unique molecular identifier. The method also includes the step of collapsing the first subset to yield a collapsed first subset sequence read, wherein the collapsing comprises eliminating sequence differences present in a minority of the sequencing reads of the first subset. The method also includes the step of identifying second sequence differences within a second subset of the plurality of sequence reads associated with a second unique molecular identifier, the second unique molecular identifier being complementary at least in part to the first unique molecular identifier. The method also includes the step of collapsing the second subset to yield a collapsed second subset sequence read, wherein the collapsing comprises eliminating sequence differences present in a minority of the sequencing reads of the second subset. The method also includes the step of determining that a sequence variant relative to a baseline in the collapsed first subset, the collapsed second subset, or a duplex of the collapsed first subset and the collapsed second subset is valid based on a function of an error rate of the genomic sequence data, wherein the error rate is determined based in part on the identified first sequence differences and the identified second sequence differences.

In an embodiment, sequencing device configured to identify sequence variants in genomic sequence data of a biological sample is provided. The device includes a memory device including executable application instructions stored therein and a processor configured to execute the application instructions stored in the memory device. The application instructions comprise instructions that cause the processor to receive genomic sequence data of a biological sample, wherein the genomic sequence data comprises a plurality of sequence reads, each sequence read being associated with a unique molecular identifier of a plurality of unique molecular identifiers; identify a plurality of errors in the genomic sequence data based on sequence disagreement between sequence reads associated with each unique molecular identifier of the plurality of unique molecular identifiers to generate an error rate of the genomic sequence data; identify a plurality of potential sequence variants in the genomic sequence data relative to a reference sequence; and determine a validity of the plurality of potential sequence variants based at least in part on the error rate.

DRAWINGS

FIG. 10 is a table showing sensitivity and specificity results relative to a default decision tree technique.

DETAILED DESCRIPTION

Figure 1:
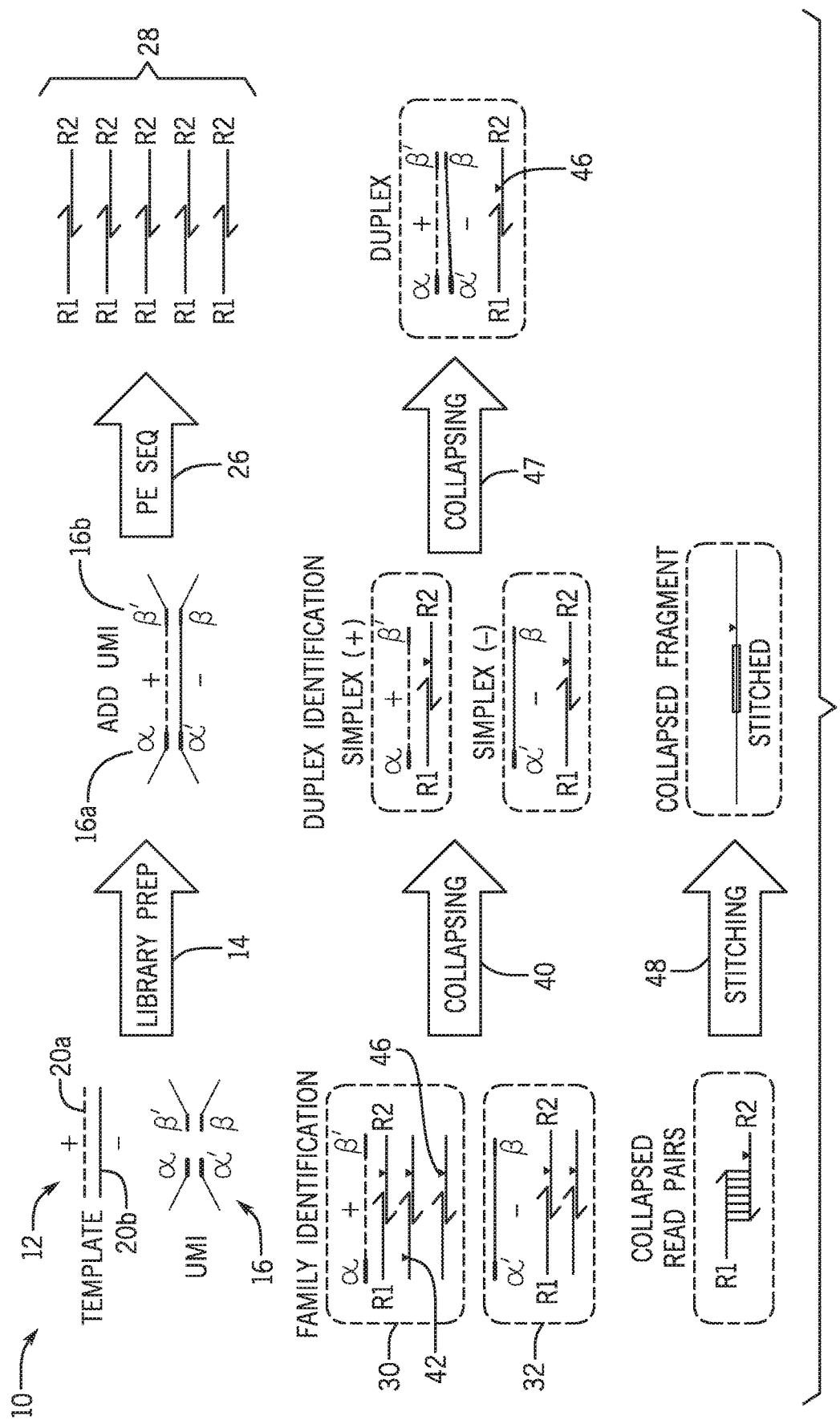
FIG. 1 is a diagrammatical overview of a workflow for identifying a genomic sequence error rate in accordance with the present techniques.

The present techniques are directed to analysis and processing of sequencing data for improved sequence variation detection and/or validation. To that end, the disclosed techniques eliminate or reduce designation of false positive sequence variants and also permit improved limits of detection of sequence variants for certain samples. FIG. 1 is a schematic workflow diagram 10 showing a sample preparation and sequence acquisition workflow.

A template 12 derived from a biological sample of interest, undergoes library preparation (step 14) to incorporate one or more UMIs 16. The template 12 may represent a plurality of nucleic acid fragments. Each template 12 incorporates an individual UMI 16 (which may include one or more identifier sequences) of a plurality of UMIs, such that the different source templates 12 are each associated with distinguishable UMIs 16 have different sequences. For example, the depicted diagram 10 is shown in the context of forked paired-end sequencing adapters including unique molecular identifiers (UMIs) 16 configured to couple to the 5' and 3' ends of a nucleic acid template fragment 12 and such that the template 12 is flanked by different portions 16a, 16b of the UMI 16. Further, the positive strand 20a includes a first UMI sequence or sequences while the negative strand 20b includes a second UMI sequence complementary to the first. The first UMI sequence and the second UMI sequence may be considered to be part of a single UMI 16 or different UMIs 16. By identifying the complementary sequences of the UMI or UMIs 16, the sequences of the positive strand 20a and the negative strand 20b may be associated with one another.

Subsequent to library preparation, genomic sequence data of the sample (including a plurality of templates 12) is acquired by any suitable sequencing technique, depicted here as paired-end sequencing (step 26). Paired-end sequencing yields a plurality of sequence reads 28, which may be in turn divided or separated by template source via the respective UMIs 16. For example, a first read group 30 including a first subset of the acquired sequence reads 28 may be associated with a first UMI 16 while a second read group 32 including a second subset of the acquired sequence reads 28 may be associated within a second UMI 16 complementary to the first UMI 16. As noted, the complementary UMIs may also be considered to be a single UMI.

Generally, sequence reads on the same strand within a single read group (e.g., the first read group 30, the second read group 32) should be identical to one another, as the associated UMI 16 links a subset of the sequence reads 28 to a single source template 12. Deviation or differences within the group are indicative of sample preparation or sequence acquisition errors. Identification and elimination of outlier reads within a read group to collapse the read group to a consensus sequence or collapsed sequence (step 40) may serve to prevent introduced sequence errors from propagating into the sequence data to yield false positive variants. As provided herein, such outlier differences, such as difference 42, that are not present in other sequence reads within the first read group 30, may be considered to be due to sequence error. Any identified differences or variations within a read group are provided as input to determining an overall error rate for the sample.

Any differences that pass through consensus sequence building, e.g., difference 46, may further be compared to sequence reads associated with a complementary strand of the UMI 16. That is, the sequences of the first read group 30 and the second read group 32 may be assembled as a duplex. Again, any differences between the groups 30, 32 may be identified before a consensus duplex of the complementary strands is assembled (step 47). Such differences may also be tracked as part of the error rate. In addition, the collapsed simplex or duplex groups may be stitched together at overlapping regions (step 48) to generate a collapsed longer fragment as part of sequence assembly. Stitching may be used to determine a frequency of any potential sequence variants.

Figure 2:
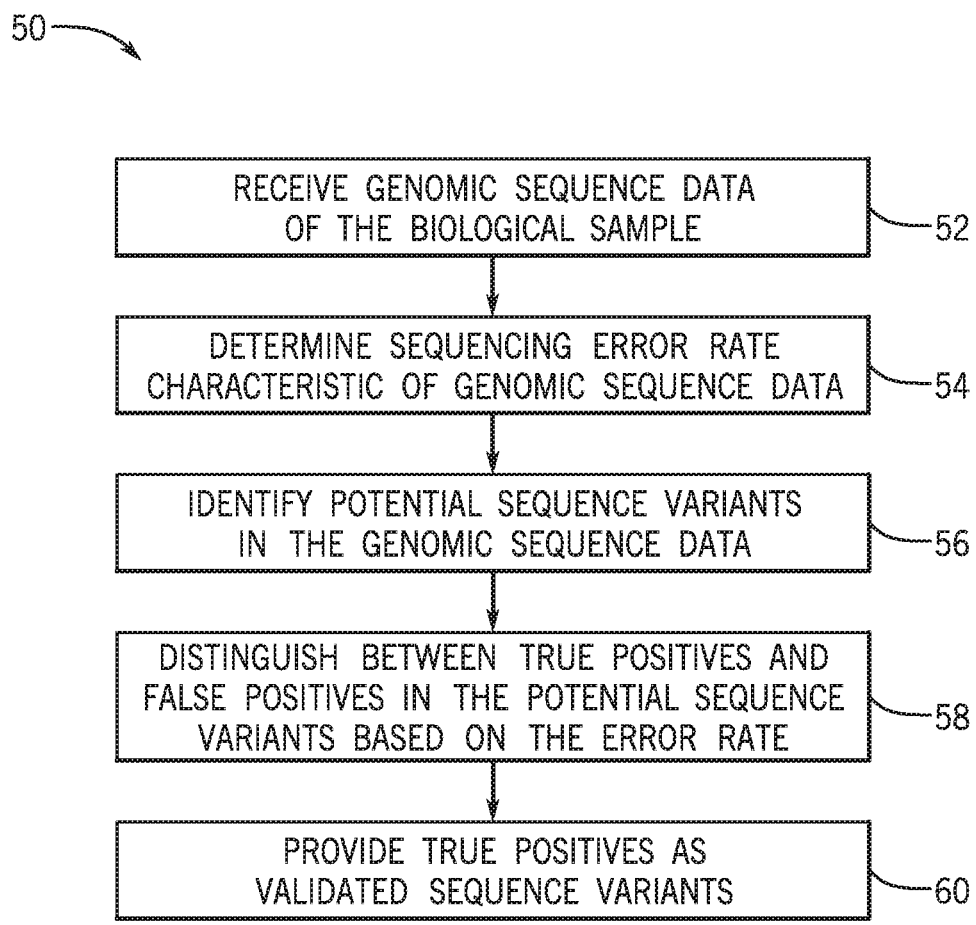
FIG. 2 is a flow diagram of a technique for sequence variant validation in accordance with the present techniques.

While the depicted diagram shows a single template 12 (e.g., a nucleic acid fragment), the disclosed techniques track error throughout the genomic sequence data to generate a global or overall error rate or rates. In particular, FIG. 2 is a flow diagram of a method 50 of receiving genomic sequence data of a biological sample, wherein the genomic sequence data comprises a plurality of sequence reads, each sequence read being associated with a unique molecular identifier of a plurality of unique molecular identifiers; The method includes the step of receiving genomic sequence data of an individual biological sample (block 52).

The received sequence data may be received subsequent to sample preparation and sequencing of the biological sample as provided herein. Further, the received genomic sequence data may be stored or retrospective sequence data. The genomic sequence data may include include customer information, biological sample organism information, biological sample type information (e.g. information identifying whether the sample is fresh, frozen, or preserved), tissue type, sequence device type, and sequencing assay type (whole genome, targeted panel).

The genomic sequence data is operated on to determine an error rate of the genomic sequence data (block 54). The error rate is characteristic of the sample itself and its associated genomic sequence data. Accordingly, the error rate may be calculated de novo for each sequencing run of a biological sample of interest. An error rate for samples taken from a same individual at different times may exhibit different characteristic error rates that depend on sample preparation variabilities, sequencing device settings, etc.

The method may also identify potential sequence variants in the genomic sequence date (block 56). Potential sequence variants may be identified relative to a reference sequence. Potential sequence variant identification may include locus mapping of sequence reads and assignment to corresponding genetic loci. The sample reads may be assigned to corresponding genetic loci based on the sequence of the nucleotides of the sample read or, in other words, the order of nucleotides within the sample read (e.g., A, C, G, T). Based on this analysis, the sample read may be designated as including a possible variant/allele of a particular genetic locus. The sample read may be collected (or aggregated or binned) with other sample reads that have been designated as including possible variants/alleles of the genetic locus. The sample reads may be analyzed to locate one or more identifying sequences (e.g., UMIs 16) of nucleotides that differentiate the sample read from other sample reads.

The mapped sample reads are analyzed relative to the reference sequence to identify potential sequence variants. Among other things, the results of the analysis identify the potential variant call, a sample variant frequency, a reference sequence and a position within the genomic sequence of interest at which the variant occurred. For example, if a genetic locus is known for including SNPs, then the assigned reads that have been called for the genetic locus may undergo analysis to identify the SNPs of the assigned reads. If the genetic locus is known for including polymorphic repetitive DNA elements, then the assigned reads may be analyzed to identify or characterize the polymorphic repetitive DNA elements within the sample reads. In some embodiments, if an assigned read effectively matches with an STR locus and an SNP locus, a warning or flag may be assigned to the sample read. The sample read may be designated as both an STR locus and an SNP locus. The analyzing may include aligning the assigned reads in accordance with an alignment protocol to determine sequences and/or lengths of the assigned reads. The alignment protocol may include the method described in International Application No. PCT/US2013/030867 (Publication No. WO 2014/142831), filed on Mar. 15, 2013, which is herein incorporated by reference in its entirety. The analysis may also count a number of reads having a particular potential variant allele relative to a total coverage for a particular locus.

Once identified, the potential sequence variants are operated on by a function that takes into account the determined error rate to distinguish between true positives and false positives (block 58). In on embodiment, for individual potential sequence variant, a likelihood score is determined based on a likelihood ratio:

Likelihood ratio (L)=Likelihood (observed variant is error-r|overage, error rate)/Likelihood (observed variant is true positive|overage, variant allele frequency), where the variant allele frequency (VAF)=max (observed VAF, limit of detection).

The likelihood score is a function of the error rate, the read coverage at the particular site, and the frequency that the potential sequence variant occurs in the reads. For example, lower frequency variants may be less likely to be validated. The likelihood score or ratio may have adjustable thresholds that are set by the user or the system based on user inputs and/or sample type. Potential sequence variants may be validated based on a likelihood score above or below a threshold or within a range. For example, a likelihood score or ratio below 0.01 and above 0.0001 or between $10^{-6}$ to $10^{-2}$ may be indicative of a pass. In another embodiment, the thresholds may be set based on a calculated specificity goal.

Once identified, the validated sequence variants may be provided (block 60) to a user. For example, the validated sequence may be provided as a generated report, e.g., stored as a report file or displayed on a graphical user interface for user interaction. Alternatively, when the validation operation invalidates or disqualifies potential variant call, the validation operation may also report or store a corresponding indication (e.g., a negative indicator, a no call indicator, an in-valid call indicator) as part of the report. The validation also may provide the likelihood score related to a degree of confidence that the variant call is correct or the invalid call designation is correct.

Figure 3:
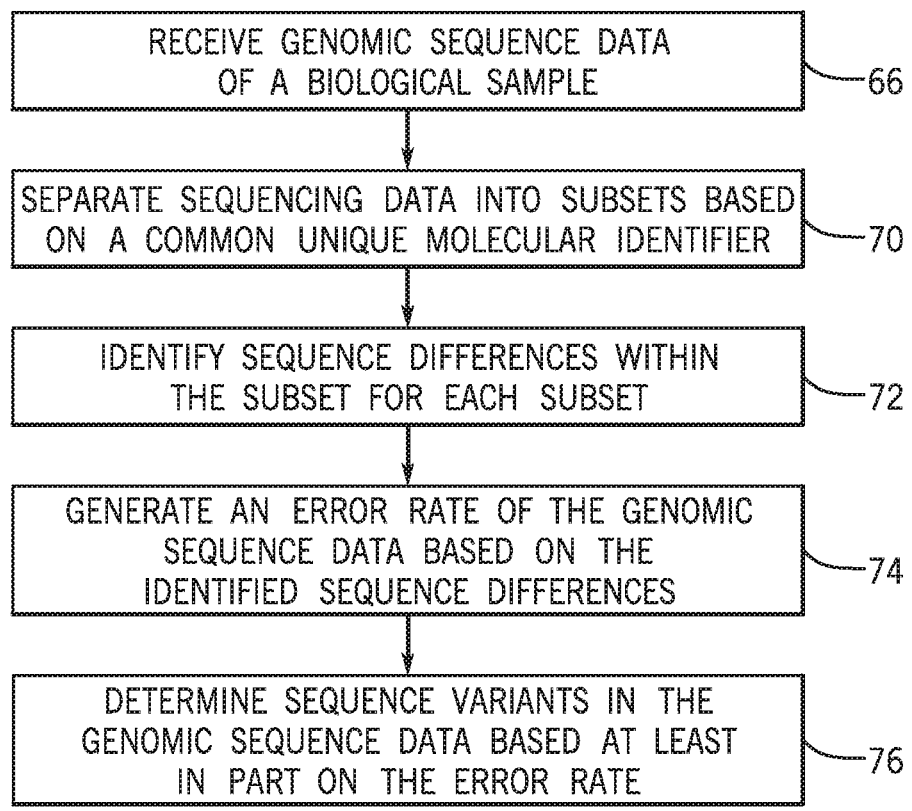
FIG. 3 is a flow diagram of a technique for sequence variant identification in accordance with the present techniques.

FIG. 3 is a flow diagram of a method 64 that operates on received genomic sequence data of a biological sample (block 66) to determine sequence variants. The genomic sequence data includes sequences of UMIs, whereby each sequence read is associated with one UMI of a plurality of UMIs used in the sequencing run. The sequence reads may be separated into read groups, whereby each read group is a subset of the sequence reads that are associated with a common UMI (block 70). Accordingly, each sequence read should be present in only one read group. Once separated, errors in the genomic sequence data are identified based on sequence disagreement between the subset of sequence reads within the read group. Each sequence read for a particular UMI should be identical. Further, for paired end sequencing, sequenced strands in both directions should align. The presence of sequence variability within a particular read group is indicative of systemic error. Accordingly, based on the overall errors identified within each different read group (block 72), an overall error rate of the genomic sequence data may be determined (block 74). The error rate may in turn be used to identify and/or validate sequence variants in the genomic sequence data (block 76).

Figure 4:
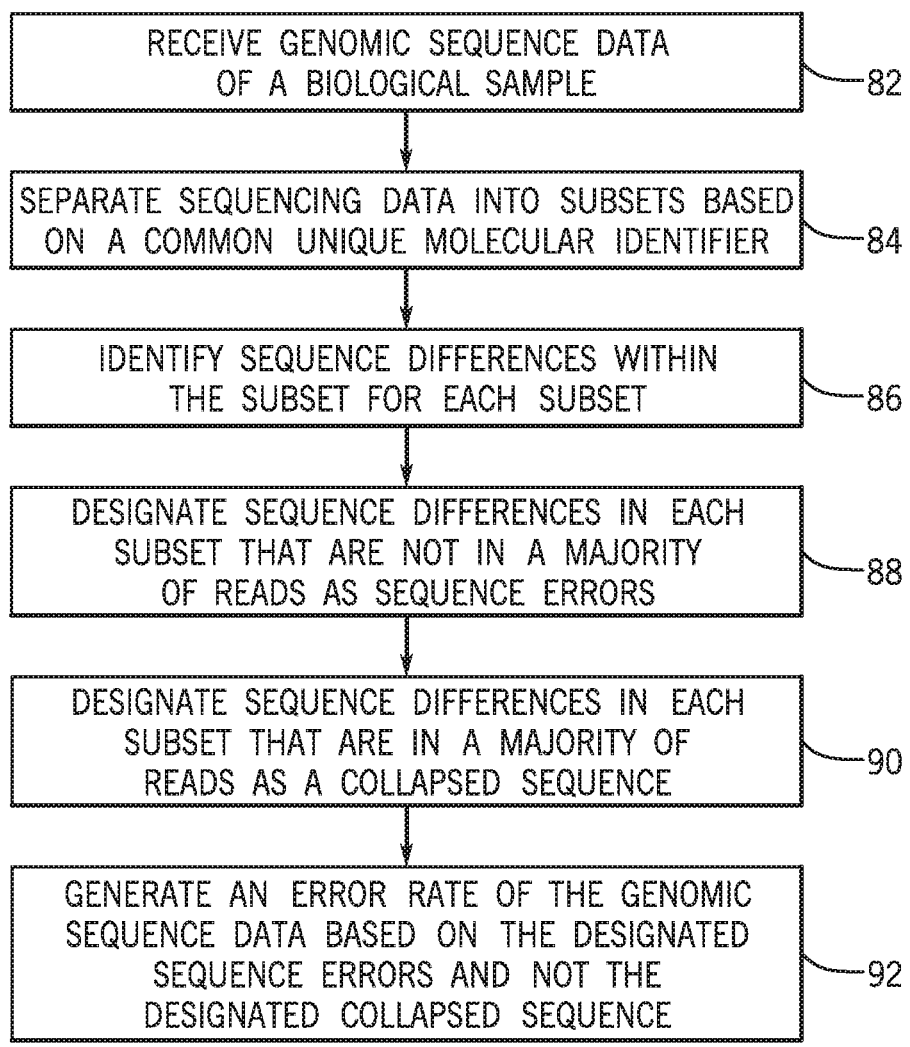
FIG. 4 is a flow diagram of a technique for determining a genomic sequence data error date in accordance with the present techniques.

FIG. 4 is a flow diagram of a method 80 for generating an error rate as provided herein. The method 80 operates on received genomic sequence data of a biological sample (block 82) that has been separated into subsets based on a common unique molecular identifier (block 84). As part of generating a consensus or collapsed sequence, sequence differences within the subset are identified (block 86). The collapsed sequence may be determined based on a majority voting rule, whereby sequence differences that are in a minority of sequence reads in a particular subset (i.e., read group) are designated as sequence errors (block 88) but sequence differences that are in a majority of the sequence reads pass through to build the consensus or collapsed sequence (block 90). Based on the identified sequence errors, the error rate is identified (block 92). However, not all sequence differences in each subgroup necessarily contribute to the error rate. Sequence differences in the majority of sequence reads (see difference 46 of FIG. 1) are distinguished from sequence differences in the minority.

Figure 5:
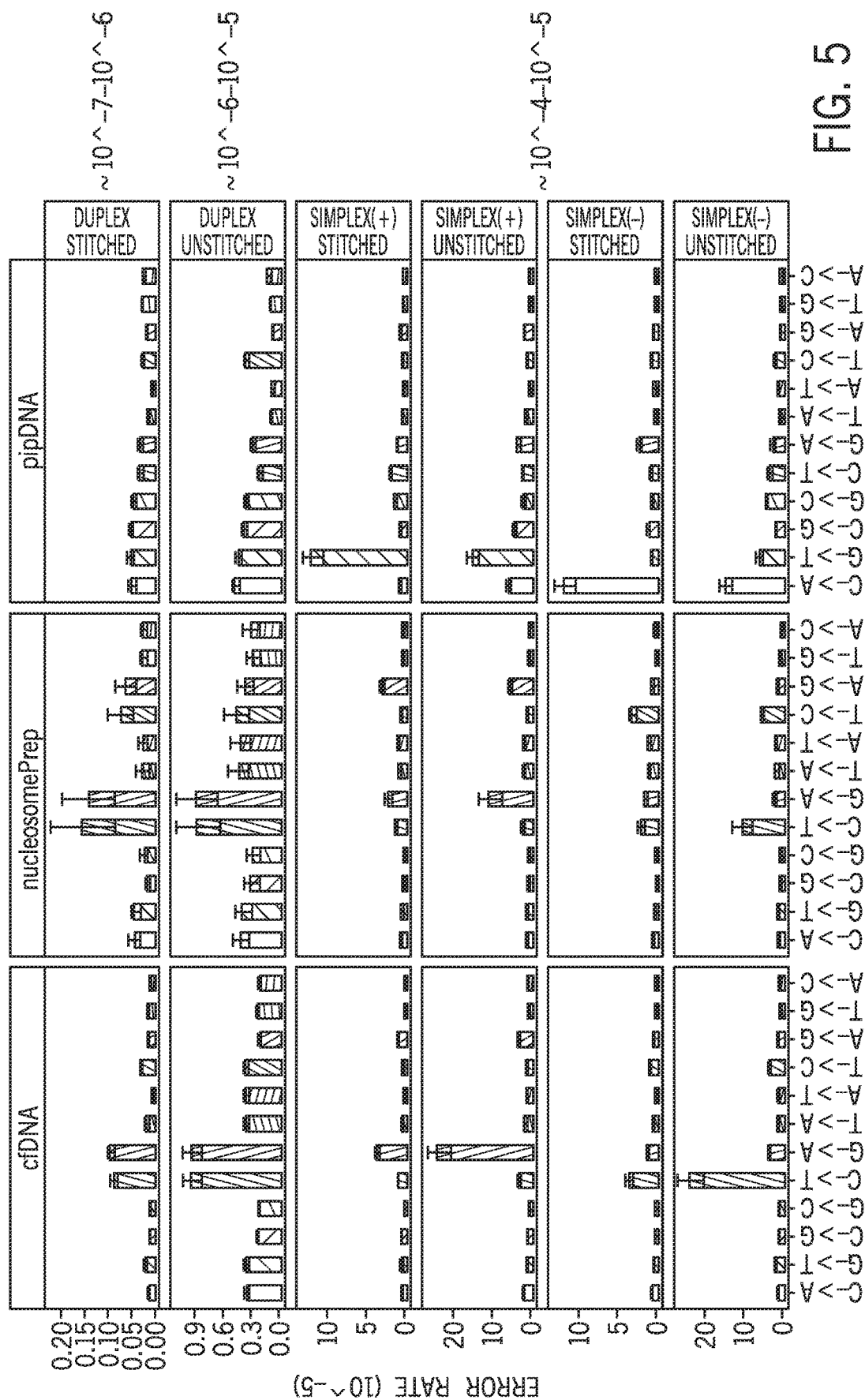
FIG. 5 shows stratified error rates for a variety of source samples and error types.

While certain embodiment are disclosed in the context of a global or overall error rate for genomic sequence data, the error rate may, additionally or alternatively, be stratified based on a type of nucleotide change. In this manner, systemic error that is biased towards particular nucleotide changes is identified. FIG. 5 is a panel of error rates separated out by type of change. The error rates are compared between different sample types, including 24 single cell free DNA (cfDNA) BRN samples, nucleosome prep of seven cancer cell lines and 6 0.2% zoo mix samples, and genomic pipDNA including three healthy samples and 21 HD753 titrated samples. Further, the inputs to the error rate determination are separated by duplex, simplex, stitched, and unstitched sequence reads in various combination. As noted with reference to FIG. 1, duplex building and stitching corrects errors in template sequences by eliminating sequence differences that are associated with error.

As observed, the error rates of each type of error vary based on sample type. For example, in cell free DNA and nucleosomePrep, deamination and resultant G to A errors are present in relatively higher levels. Oxidation is dominant in pipDNA, resulting in observed higher error rates of G to T changes. Accordingly, in certain embodiments, certain biological sample types may be associated with particular characteristic errors. In one embodiment, the sequence variant determination may include a weighting factor to weigh against potential variants that are associated with error for the sample type in question.

Figure 6:
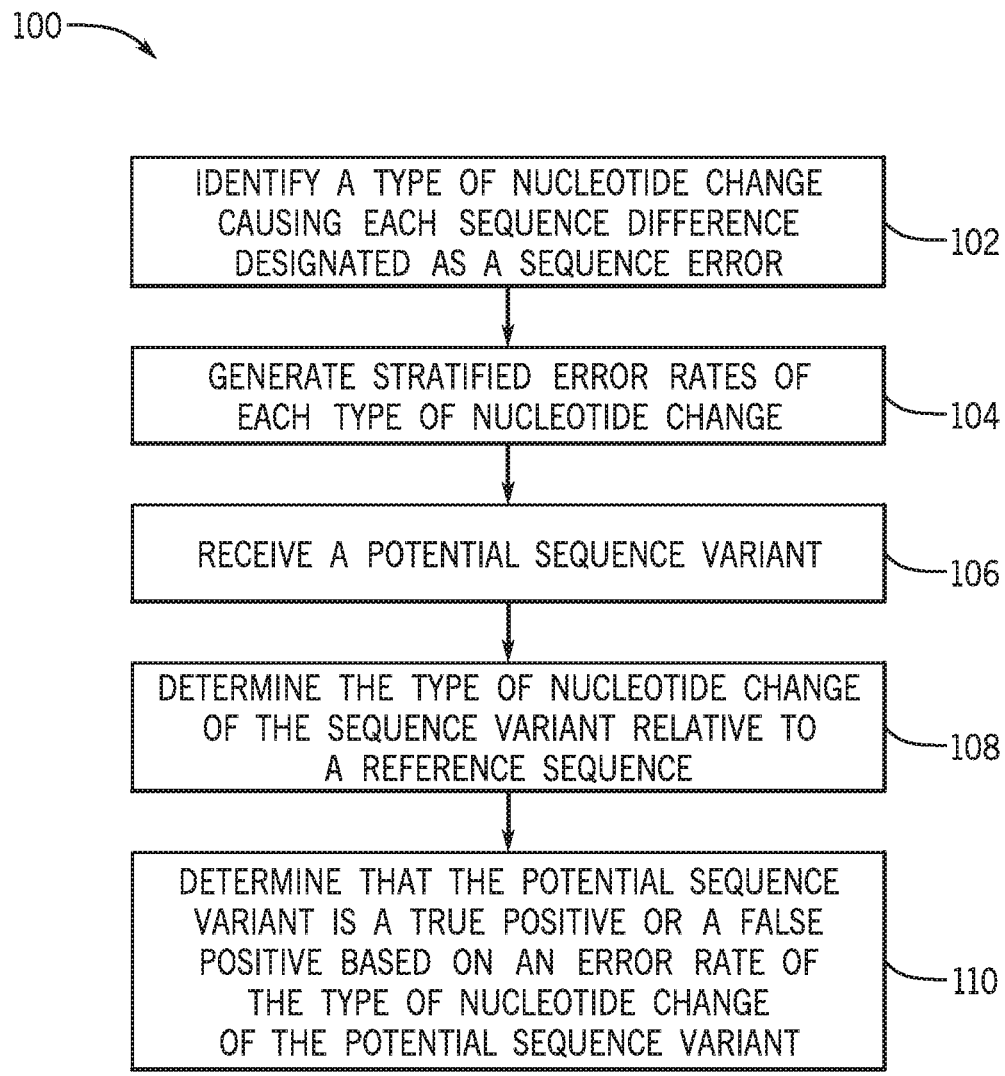
FIG. 6 is a flow diagram of a technique for determining stratified error rates and sequence variant validation in accordance with the present techniques.

FIG. 6 is a flow diagram of a method 100 of determining stratified error rates, as shown in FIG. 5. For sequence reads that are part of a single read group, individual reads having sequence differences within the group and in a minority of strands are eliminated to correct the template. These eliminated sequence reads may be further analyzed to identify the types of erroneous sequence changes that occur at each locus (block 102). The nucleotide change forming the erroneous sequence change is considered relative to the majority sequence read in the group to identify the type of nucleotide change. For example, if the majority sequence read includes a G at position (n) of the read, and the minority read or reads include an A at position (n), the type of change may be binned as a G>A change. The change may be a single nucleotide change or an indel. This process is applied to all individual read groups including minority sequence reads having sequence differences to generate stratified error rates of each type of nucleotide change throughout the genomic sequence data (block 104), whereby the nucleotide changes are based on disagreement within the genomic sequence data itself. Using the stratified error rates, a potential sequence variant may be validated. Once received (block 106) as part of a variant identification operation, the potential sequence variant in the genomic sequence data is classified according to the type of nucleotide change relative to a reference sequence (block 108). In particular, while the error rates are calculated using a measure internal to the genomic sequence data (internal sequence disagreement between sequence reads of a read group as provided herein), the sequence variants are determined relative to a reference sequence. If the potential variant sequence is a G>A change relative to the reference sequence, the G>A error rate (and not the other error rates for the other types of nucleotide changes) are used to determine that the potential sequence variant is a true positive or a false positive (block 110), e.g., as part of a likelihood ratio determination. In this manner, a biological sample having a relatively low G>A error rate may validate a G>A sequence variant while the same biological sample, with a relatively high G>T error rate may apply more stringent conditions to validating potential G>T sequence variants. In one embodiment, a weighting factor for each type of error may be generated based on the stratified error rates.

Figure 7:
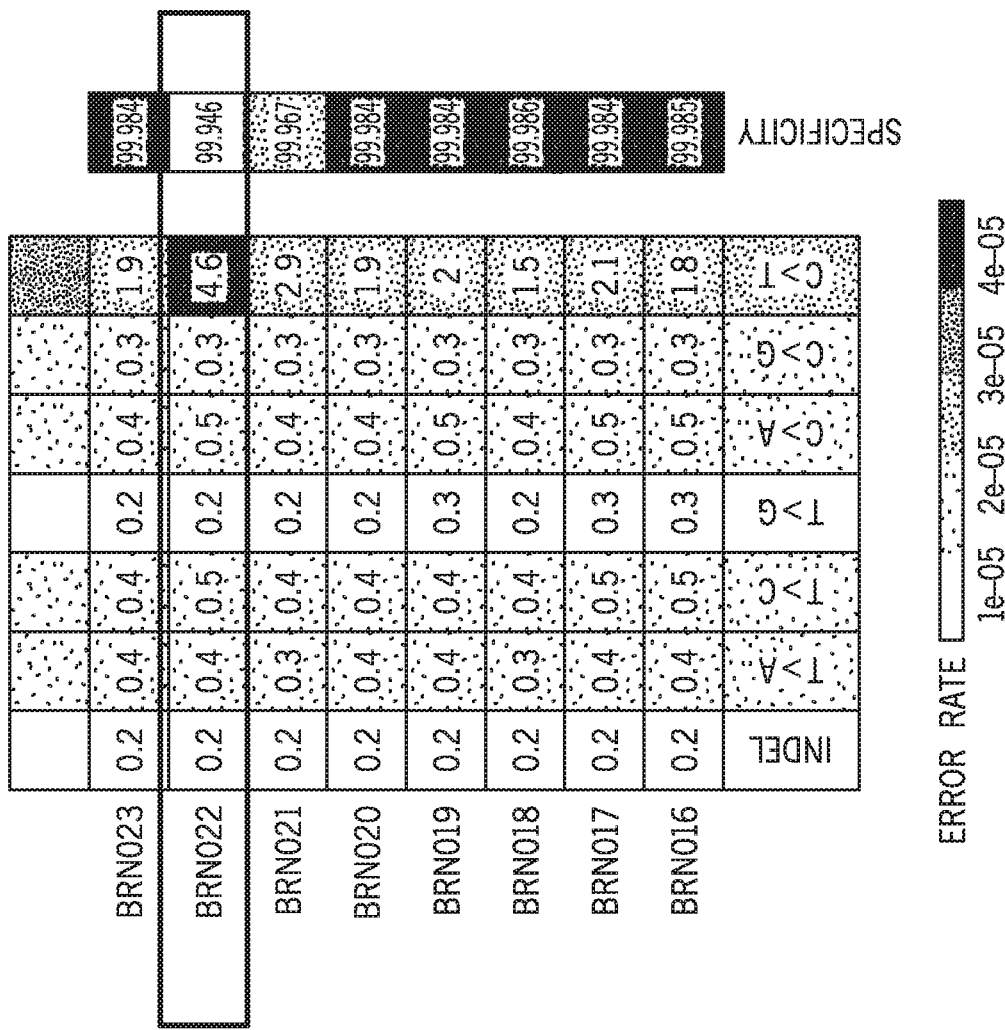
FIG. 7 shows stratified error types for source samples, including a sample with a high error rate.

FIG. 7 shows a comparison of error rates in different cell free DNA samples relative to one another and associated specificity of sequence variant identification of each sample. The highlighted sample, BRN022, exhibits a significant increase in C>T errors relative to the sample cohort. However, the sample cohort generally shows relatively higher C>T errors relative to other error types, which are indicative of C>T or G>A deamination changes. Nonetheless, the specificity in the sample with high C>T or G>A error rates is about or greater than 99.95%, indicating a high specificity in the context of a biological sample and genomic sequence data having a high sequence error rate.

Figure 8:
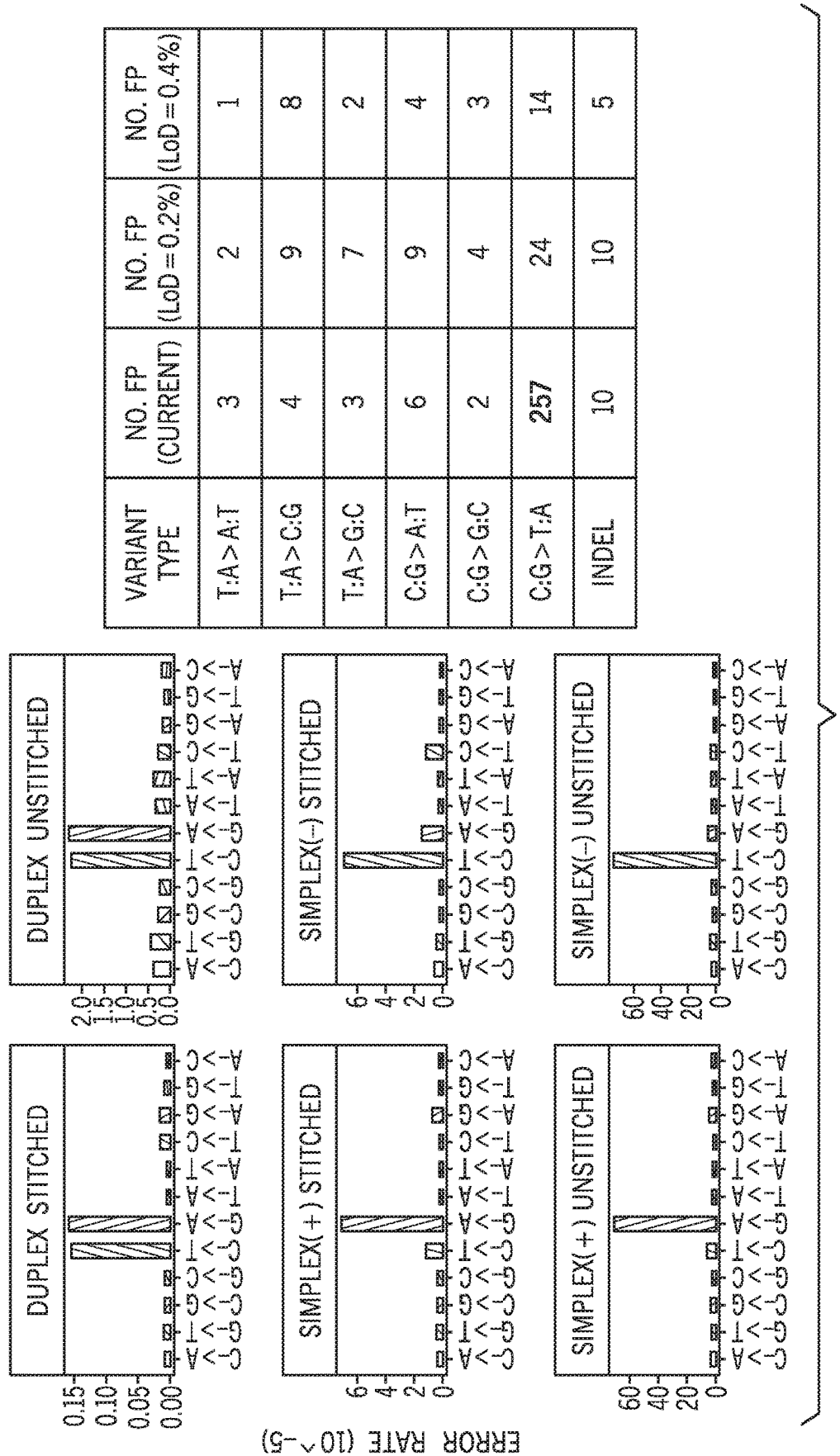
FIG. 8 shows stratified error rates for a variety of error types for the high error rate sample of FIG. 7.

FIG. 8 shows stratified error rates for a variety of error types for the high error rate sample of FIG. 7 for duplex and simplex (positive and negative) data, stitched and unstitched. The template correction in the stitched data appears to be associated with different error identification relative to the unstitched data. However, the positive and negative strand errors appear to correlate, with the C>T error appearing as G>A in the opposing strand. Similarly, the identified peak in T>C error appears as a peak in A>G error in the opposing strand. The identified high error C>T and G>A changes are examined relative to a default technique that does not calculate error rate as provided herein. The default technique identified 257 C>T and G>A false positives in the BRN022 sample, while the stratified error rate method identified 24 and 14 (depending on the limit of detection thresholds), showing a significant decrease in false positive identification for a high error rate sample.

Figure 9:
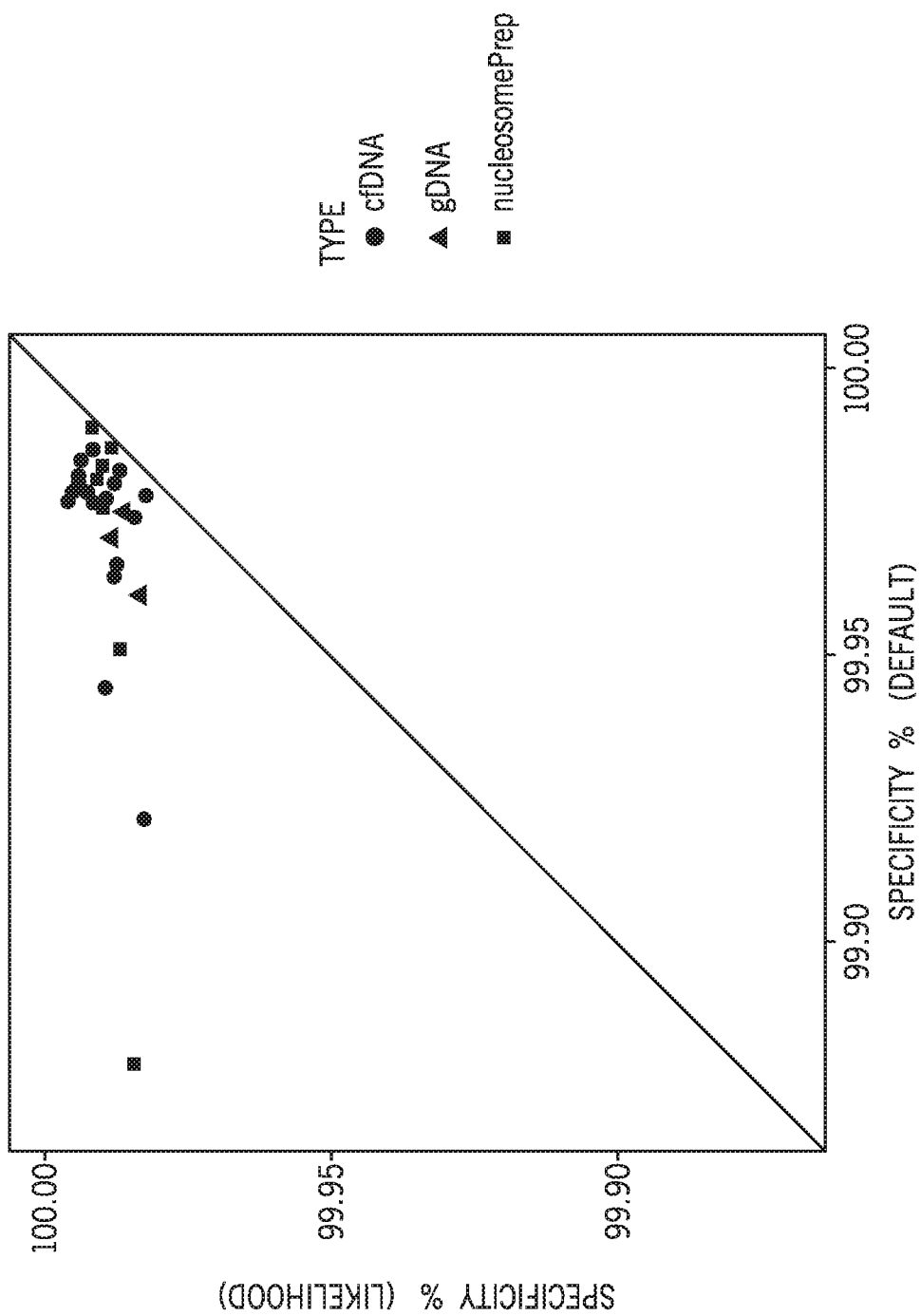
FIG. 9 is a plot showing improved specificity relative to a decision tree technique.

FIG. 9 is a plot showing improved specificity relative to a decision tree technique. Such a technique may be a technique as provided in PCT publication WO2018093780 and that involves one or more quality scores based on weighting fragment types. In contrast to the decision tree technique, the disclosed techniques may determine error rates on an per-sample basis rather than using a predetermined weighting factor. For example, certain samples may exhibit higher error in positive strands vs. negative strands. Accordingly, the error may also be stratified based on fragment type as calculated de novo. As shown in FIG. 9, the error rate techniques as provided herein, the likelihood model, result in higher specificity relative to a decision tree technique for all three sample types examined. FIG. 10 is a table showing sensitivity and specificity results relative to a default decision tree technique for the nucleosomePrep samples, including a percentage of zoo mix, showing sensitivity in line with the decision tree technique. The likelihood (based on error rate) technique exhibits high specificity, indicating an improvement in variant calling and a reduction in false positive identification.

Figure 11:
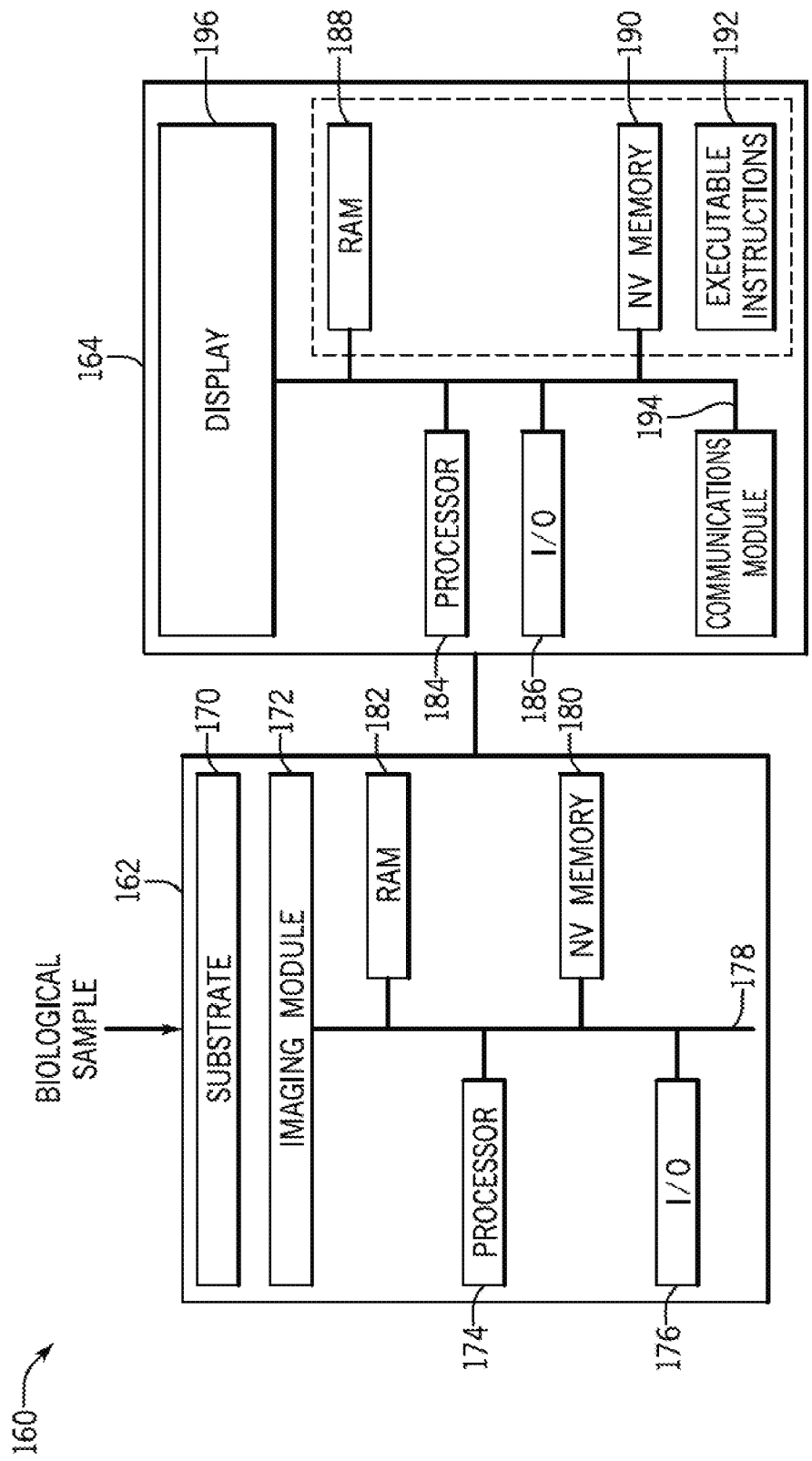
FIG. 11 is a block diagram of a sequencing device in accordance with the present techniques.

FIG. 11 is a schematic diagram of a sequencing device 160 that may be used in conjunction with the disclosed embodiments for acquiring sequencing data that is used to identify and/or validate sequence variant calls as provided herein. The sequence device 160 may be implemented according to any sequencing technique, such as those incorporating sequencing-by-synthesis methods described in U.S. Patent Publication Nos. 2007/0166705; 2006/0188901; 2006/0240439; 2006/0281109; 2005/0100900; U.S. Pat. No. 7,057,026; WO 05/065814; WO 06/064199; WO 07/010,251, the disclosures of which are incorporated herein by reference in their entireties. Alternatively, sequencing by ligation techniques may be used in the sequencing device 160. Such techniques use DNA ligase to incorporate oligonucleotides and identify the incorporation of such oligonucleotides and are described in U.S. Pat. Nos. 6,969,488; 6,172,218; and 6,306,597; the disclosures of which are incorporated herein by reference in their entireties. Some embodiments can utilize nanopore sequencing, whereby target nucleic acid strands, or nucleotides exonucleolytically removed from target nucleic acids, pass through a nanopore. As the target nucleic acids or nucleotides pass through the nanopore, each type of base can be identified by measuring fluctuations in the electrical conductance of the pore (U.S. Pat. No. 7,001,792; Soni & Meller, *Clin. Chem.* 53, 1996-2001 (2007); Healy, *Nanomed.* 2, 459-481 (2007); and Cockroft, et al. *J. Am. Chem. Soc.* 130, 818-820 (2008), the disclosures of which are incorporated herein by reference in their entireties). Yet other embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety. Particular embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides, or with zero-mode waveguides as described, for example, in Levene et al. Science 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference in their entireties. Other suitable alternative techniques include, for example, fluorescent in situ sequencing (FISSEQ), and Massively Parallel Signature Sequencing (MPSS). In particular embodiments, the sequencing device 160 may be a HiSeq, MiSeq, or HiScanSQ from Illumina (La Jolla, CA). In other embodiment, the sequencing device 160 may be configured to operate using a CMOS sensor with nanowells fabricated over photodiodes such that DNA deposition is aligned one-to-one with each photodiode.

The sequencing device 160 may be "one-channel" a detection device, in which only two of four nucleotides are labeled and detectable for any given image. For example, thymine may have a permanent fluorescent label, while adenine uses the same fluorescent label in a detachable form. Guanine may be permanently dark, and cytosine may be initially dark but capable of having a label added during the cycle. Accordingly, each cycle may involve an initial image and a second image in which dye is cleaved from any adenines and added to any cytosines such that only thymine and adenine are detectable in the initial image but only thymine and cytosine are detectable in the second image. Any base that is dark through both images in guanine and any base that is detectable through both images is thymine. A base that is detectable in the first image but not the second is adenine, and a base that is not detectable in the first image but detectable in the second image is cytosine. By combining the information from the initial image and the second image, all four bases are able to be discriminated using one channel.

In the depicted embodiment, the sequencing device 160 includes a separate sample processing device 162 and an associated computer 164. However, as noted, these may be implemented as a single device. Further, the associated computer 164 may be local to or networked with the sample processing device 162. In the depicted embodiment, the biological sample may be loaded into the sample processing device 162 on a sample substrate 170, e.g., a flow cell or slide, that is imaged to generate sequence data. For example, reagents that interact with the biological sample fluoresce at particular wavelengths in response to an excitation beam generated by an imaging module 172 and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As will be appreciated by those skilled in the art, the wavelength at which the dyes of the sample are excited and the wavelength at which they fluoresce will depend upon the absorption and emission spectra of the specific dyes. Such returned radiation may propagate back through the directing optics. This retrobeam may generally be directed toward detection optics of the imaging module 172.

The imaging module detection optics may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860, which is incorporated herein by reference. Other useful detectors are described, for example, in the references provided previously herein in the context of various nucleic acid sequencing methodologies.

The imaging module 172 may be under processor control, e.g., via a processor 174, and the sample receiving device 162 may also include I/O controls 176, an internal bus 78, non-volatile memory 180, RAM 182 and any other memory structure such that the memory is capable of storing executable instructions, and other suitable hardware components that may be similar to those described with regard to FIG. 11. Further, the associated computer 164 may also include a processor 184, I/O controls 186, a communications module 184, and a memory architecture including RAM 188 and non-volatile memory 190, such that the memory architecture is capable of storing executable instructions 192. The hardware components may be linked by an internal bus 194, which may also link to the display 196. In embodiments in which the sequencing device 160 is implemented as an all-in-one device, certain redundant hardware elements may be eliminated.

The processor 184 may be programmed to operate on the genomic sequence data as provided herein. In particular embodiments, based on the image data acquired by the imaging module 172, the sequencing device 160 may be configured to generate sequencing data that includes base calls for each base of a sequence read. Further, based on the image data, even for sequence reads that are performed in series, the individual reads may be linked to the same location via the image data and, therefore, to the same template strand. The processor 184 may also be programmed to perform downstream analysis on the sequences corresponding to the inserts for a particular sample subsequent to assignment of sequence reads to the sample. The processor 184 may be configured to operate on sequence data in the form of a BAM file and to output the variant calls in various formats, such as in a .VCF or .GVCF file.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A computer-implemented method for sample preparation or sequence acquisition errors under control of a processor executing instructions, comprising:
    capturing image data of a biological sample using an imaging module of a sequencing device;
    generating genomic sequence data of the biological sample based on the image data, wherein the genomic sequence data comprises base calls for a plurality of sequence reads, each sequence read being associated with a unique molecular identifier of a plurality of unique molecular identifiers;
    identifying errors in the genomic sequence data based on internal sequence disagreement within a first subset of the plurality of sequence reads associated with a first unique molecular identifier, internal sequence disagreement within a second subset of the plurality of sequence reads having a second unique molecular identifier complementary to the first unique molecular identifier, or both, to generate a sample-specific error rate of the genomic sequence data associated with sequence acquisition by the sequence device of the biological sample, wherein the error rate is a global error rate based on the identified errors for the plurality of unique molecular identifiers;
    identifying a plurality of potential sequence variants in the genomic sequence data relative to a reference sequence;
    operating on the plurality of potential sequence variants using a function that takes into account the error rate of the genomic sequence data to generate a likelihood score for each potential sequence variant;
    receiving a user input via a graphical user interface of a display configured to receive the user input, wherein the user input comprises a sample type of the biological sample;
    adjusting a threshold or range based on the user input;
    classifying false positive sequence variants of the plurality of potential sequence variants based on the likelihood score for each potential sequence variant relative to the adjusted threshold or range; and
    eliminating the false positive sequence variants from the plurality of potential sequence variants to yield a plurality of sequence variants, wherein the plurality of sequence variants accounts for sequence acquisition errors.

2. The method of claim 1, wherein the error rate comprises individual error rates based on a type of nucleotide change.

3. The method of claim 2, wherein the classifying comprises applying a function of the error rate for an individual type of nucleotide change and a read coverage of an individual potential sequence variant to determine that the individual potential sequence variant is a false positive sequence variant.

4. The method of claim 1, wherein identifying errors in the genomic sequence data based on the internal sequence disagreement within the first subset of the plurality of sequence reads comprises identifying differences between a first read direction or a second read direction associated with an individual unique molecular identifier, wherein the identified differences contribute to the error rate.

5. The method of claim 4, comprising collapsing the sequence reads of the first subset to yield a collapsed first subset sequence read indicative of a majority consensus sequence of the sequence reads of the first subset.

6. The method of claim 5, wherein identifying errors in the genomic sequence data based on sequence disagreement comprises identifying second differences between the collapsed first subset sequence read and the sequence reads of the second subset, wherein the identified second differences contribute to the error rate.

7. The method of claim 6, comprising collapsing the sequence reads of the second subset and the collapsed first subset sequence read to yield a duplex collapsed sequence read indicative of a majority consensus sequence of the sequence reads of the first subset and the second subset.

8. The method of claim 7, wherein the duplex collapsed sequence read is compared to the reference sequence to identify a potential sequence variant of the plurality of potential sequence variants.

9. The method of claim 1, wherein the classifying comprises applying a function based at least in part on the error rate to each potential sequence variant to generate a score and determining a false positive or true positive classification of each potential sequence variant based on the score.

10. The method of claim 9, wherein the function is based on the error rate and a read coverage at a site of each individual potential sequence variant.

11. The method of claim 9, wherein the error rate is selected from a plurality of error rates at each potential sequence variant site based on a type of potential sequence variant, and wherein the function is based on the selected error rate and a read coverage at each individual potential sequence variant site.

12. The method of claim 9, wherein the error rate is weighted based on a type of the biological sample, and wherein the function is based on the weighted error rate and a read coverage at each individual potential sequence variant site.

13. The method of claim 1, comprising providing an indication of the plurality of sequence variants on a display.

14. The method of claim 1, wherein the error rate is independent of positive or negative strand identification.

15. The method of claim 1, comprising generating a report of plurality of sequence variants and displaying the report on the graphical user interface.

16. The method of claim 15, comprising providing the likelihood score for each of the plurality of sequence variants in the report.

17. The method of claim 15, comprising providing the eliminated false positive sequence variants with a negative or invalid sequence variant indication as part of the report.

18. A computer-implemented method for sample preparation or sequence acquisition errors under control of a processor executing instructions, comprising:
   capturing image data of a biological sample using an imaging module of a sequencing device;
   generating genomic sequence data of the biological sample based on the image data, wherein the genomic sequence data comprises base calls for a plurality of sequence reads, each sequence read being associated with a unique molecular identifier of a plurality of unique molecular identifiers;
   identifying errors in the genomic sequence data based on internal sequence disagreement within a first subset of the plurality of sequence reads associated with a first unique molecular identifier, internal sequence disagreement within a second subset of the plurality of sequence reads having a second unique molecular identifier complementary to the first unique molecular identifier, or both, to generate a sample-specific error rate of the genomic sequence data associated with sample preparation of the biological sample, wherein the error rate is a global error rate based on the identified errors for the plurality of unique molecular identifiers;
   identifying a plurality of potential sequence variants in the genomic sequence data relative to a reference sequence;
   operating on the plurality of potential sequence variants using a function that takes into account the error rate of the genomic sequence data to generate a likelihood score for each potential sequence variant;
   receiving a user input via a graphical user interface of a display configured to receive the user input, wherein the user input comprises a sample type of the biological sample;
   adjusting a threshold or range based on the user input;
   classifying false positive sequence variants of the plurality of potential sequence variants based on the likelihood score for each potential sequence variant relative to the adjusted threshold or range;
   eliminating the false positive sequence variants from the plurality of potential sequence variants to yield a plurality of sequence variants, wherein the plurality of sequence variants accounts for sample preparation errors.

* * * * *

UNITED STATES PATENT AND TRADEMARK OFFICE
CERTIFICATE OF CORRECTION

Page 1 of 1

PATENT NO. : 12,040,047 B2
APPLICATION NO. : 16/206552
DATED : July 16, 2024
INVENTOR(S) : Tingting Jiang and Chen Zhao It is certified that error appears in the above-identified patent and that said Letters Patent is hereby corrected as shown below:

In the Claims

In Column 20, Line 25, Claim 26, replace "range;" with --range; and--.

Signed and Sealed this
Thirty-first Day of December, 2024

Derrick Brent
*Acting Director of the United States Patent and Trademark Office*